(12) United States Patent
Noack

(10) Patent No.: US 9,820,833 B2
(45) Date of Patent: Nov. 21, 2017

(54) PROSTHETIC TOOTH SUPPORT

(75) Inventor: Falko Noack, Lustenau (AT)

(73) Assignee: Amann Girrbach AG, Koblach (AT)

( * ) Notice: Subject to any disclaimer, the term of this patent is extended or adjusted under 35 U.S.C. 154(b) by 798 days.

(21) Appl. No.: 14/117,466

(22) PCT Filed: Apr. 18, 2012

(86) PCT No.: PCT/AT2012/000105
§ 371 (c)(1),
(2), (4) Date: Nov. 13, 2013

(87) PCT Pub. No.: WO2012/155161
PCT Pub. Date: Nov. 22, 2012

(65) Prior Publication Data
US 2014/0087327 A1    Mar. 27, 2014

(30) Foreign Application Priority Data

May 16, 2011    (DE) .................. 10 2011 101 678

(51) Int. Cl.
| A61C 13/00 | (2006.01) |
| A61C 13/12 | (2006.01) |
| A61C 19/10 | (2006.01) |
| A61C 13/08 | (2006.01) |

(52) U.S. Cl.
CPC ...... *A61C 13/0027* (2013.01); *A61C 13/0004* (2013.01); *A61C 13/0006* (2013.01); *A61C 13/0022* (2013.01); *A61C 13/08* (2013.01); *A61C 13/12* (2013.01); *A61C 19/10* (2013.01)

(58) Field of Classification Search
CPC .......... B23P 17/00; B23P 19/00; A61C 13/00; A61C 13/0003; A61C 13/0027
See application file for complete search history.

(56) References Cited

U.S. PATENT DOCUMENTS

| 1,633,714 A | 6/1927 | Schwob | |
| 3,937,773 A * | 2/1976 | Huffman ................ | A61C 9/002 264/154 |
| 4,238,189 A * | 12/1980 | Tirino ..................... | A61C 9/002 264/16 |
| 4,481,162 A * | 11/1984 | Huffman ................ | A61C 9/002 249/127 |

(Continued)

FOREIGN PATENT DOCUMENTS

| CA | 2373891 | 9/2002 |
| CN | 101829801 | 9/2010 |

(Continued)

OTHER PUBLICATIONS

Fritsche, Gunther Dr., "CAD/CAM—experience: Biogentic Crowns Work Better", Hamburg, Germany, updated by Dr. Gunther Frtische on Jul. 26, 2010. http://www.zmk-aktuell,de/autorenliste/story/dadcam-erfahrung-biogenerische-kronen-funktionieren-besser-1/prin.html.

(Continued)

*Primary Examiner* — Lee D Wilson
(74) *Attorney, Agent, or Firm* — Volpe and Koenig, P.C.

(57) ABSTRACT

Prosthetic tooth support (1) with at least one prosthetic tooth (2), in particular with several prosthetic teeth (2), wherein a crown area (3) of the prosthetic tooth (2) or of the prosthetic teeth (2) is embedded, preferably cast, at least partially, preferably completely, in a support layer (4).

16 Claims, 4 Drawing Sheets

(56) References Cited

U.S. PATENT DOCUMENTS

| | | | | |
|---|---|---|---|---|
| 4,583,947 | A * | 4/1986 | Hazar | A61C 13/00 264/18 |
| 5,782,632 | A | 7/1998 | Foser | |
| 6,079,981 | A | 6/2000 | Sekendur | |
| 2002/0076530 | A1 | 6/2002 | MacDougald et al. | |
| 2002/0125619 | A1 | 9/2002 | Bodenmiller et al. | |
| 2002/0137000 | A1 | 9/2002 | Eggler | |
| 2003/0096214 | A1 | 5/2003 | Luthardt et al. | |
| 2004/0151367 | A1 | 8/2004 | Wolf et al. | |
| 2004/0219490 | A1 | 11/2004 | Gartner et al. | |
| 2006/0210944 | A1 * | 9/2006 | Jung | A61C 11/08 433/57 |
| 2007/0190492 | A1 | 8/2007 | Schmitt | |
| 2007/0287131 | A1 | 12/2007 | Ruppert et al. | |
| 2009/0287332 | A1 | 11/2009 | Adusumilli et al. | |
| 2012/0028213 | A1 * | 2/2012 | Meitner | A61C 1/084 433/74 |
| 2014/0087327 | A1 * | 3/2014 | Noack | A61C 13/0022 433/50 |
| 2015/0064644 | A1 * | 3/2015 | Scherer | A61C 9/0006 433/29 |

FOREIGN PATENT DOCUMENTS

| | | |
|---|---|---|
| DE | 403973 | 10/1924 |
| DE | 19508760 | 9/1996 |
| DE | 19532171 | 3/1997 |
| DE | 10065971 | 6/2002 |
| DE | 112007003610 | 6/2010 |
| DE | 102009003183 | 11/2010 |
| EP | 1088620 A1 | 4/2001 |
| EP | 1243233 | 9/2002 |
| EP | 1304089 | 4/2003 |
| EP | 2030590 | 3/2009 |
| EP | 1444965 | 5/2011 |
| FR | 2582932 | 12/1986 |
| WO | 9107141 | 5/1991 |
| WO | 9530382 | 11/1995 |
| WO | 2009100863 | 8/2009 |
| WO | 2013124452 | 8/2013 |

OTHER PUBLICATIONS

Web page https://xing.com/communities/posts/cad-slash-cam-erfahrung-biogenerische-kronen-funktionieren-besser-1003929758, on which page a member "Uwe Grauert" of the online-group "cerec-connect" has added the aforesaid article to his own article written on Jul. 31, 2010.

* cited by examiner

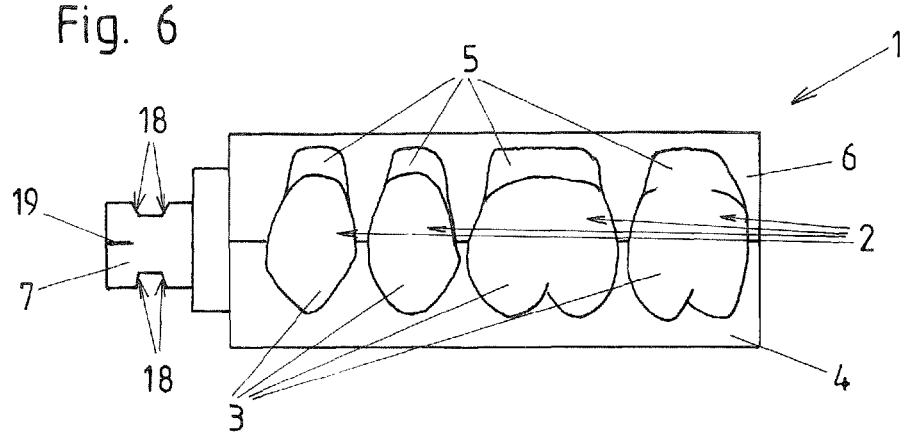
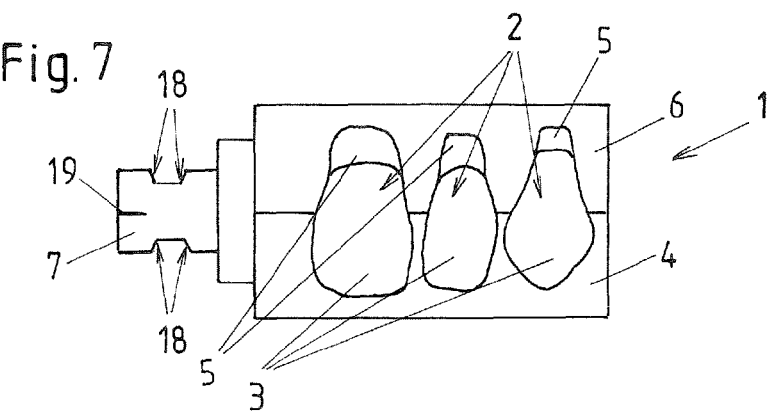
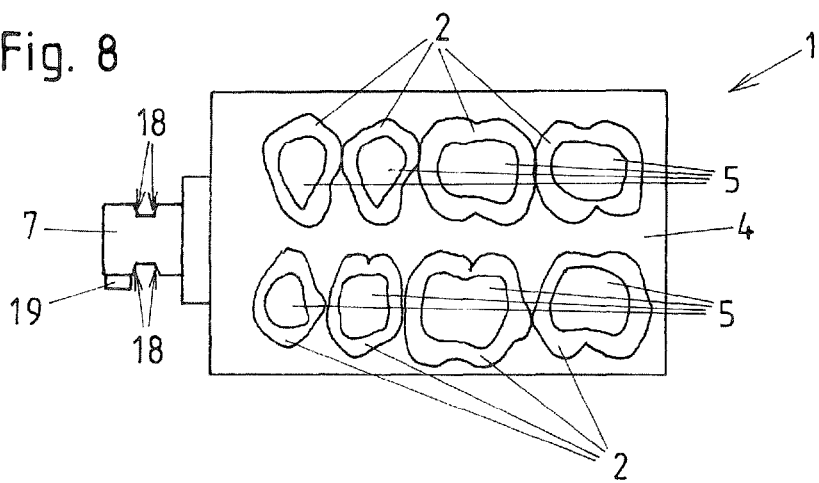

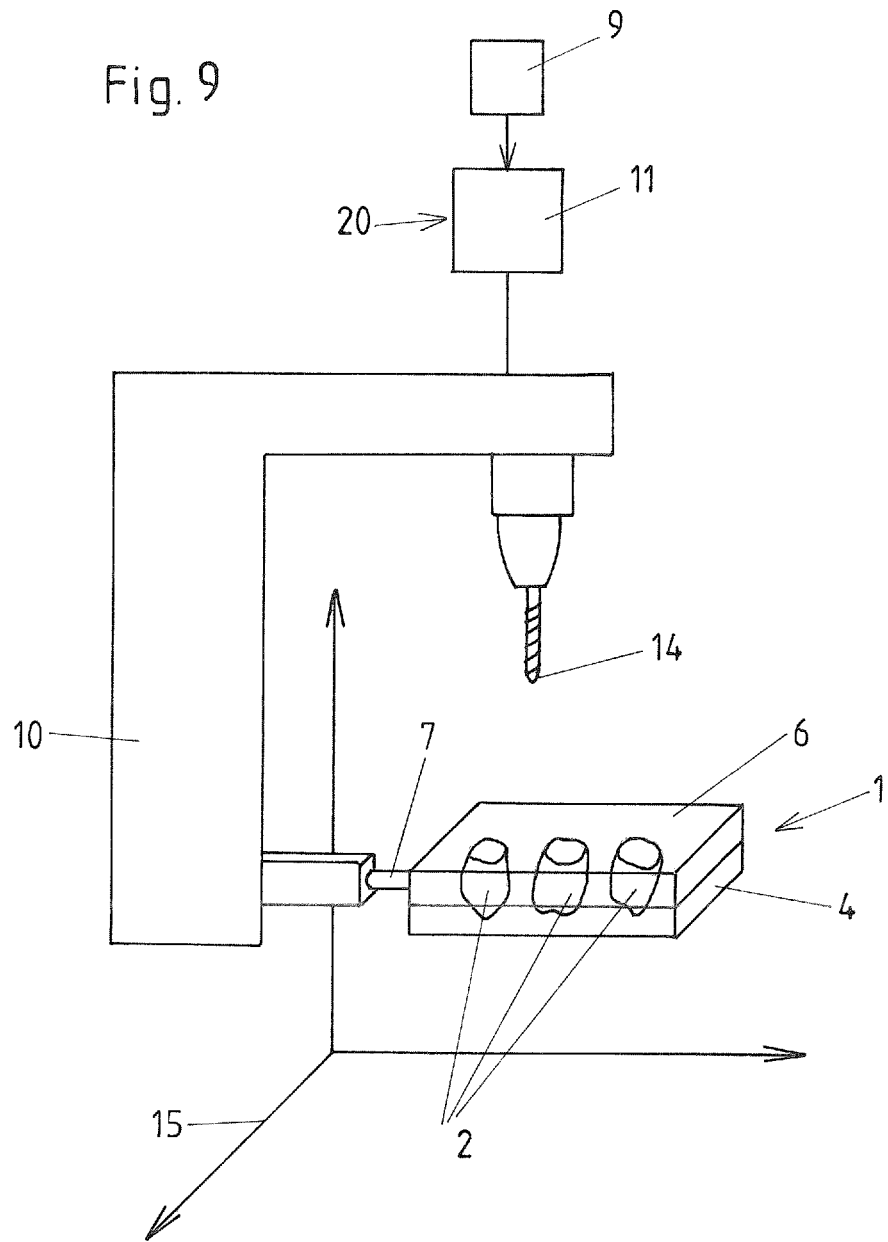

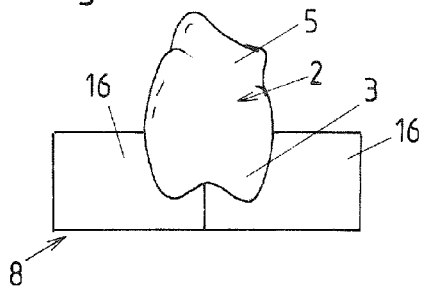
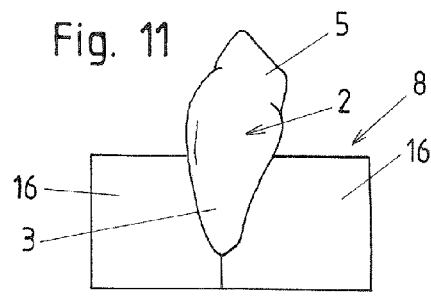
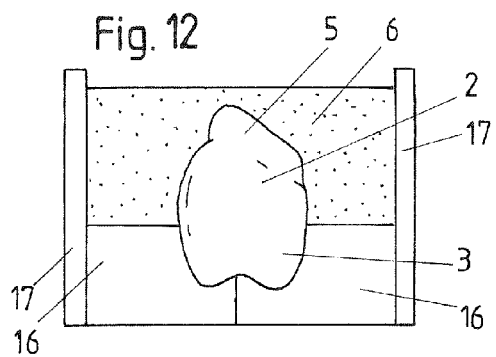
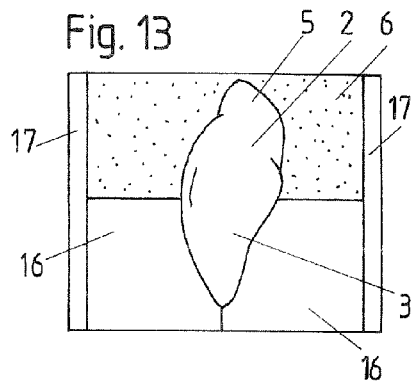
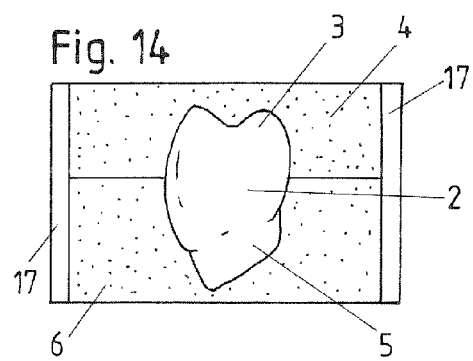
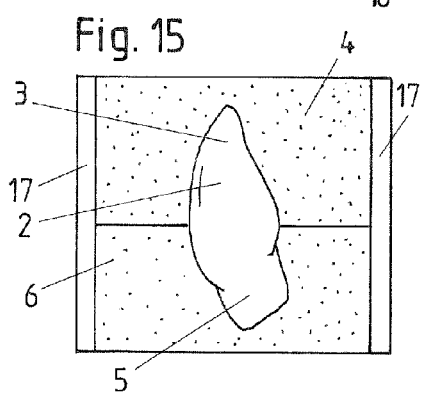
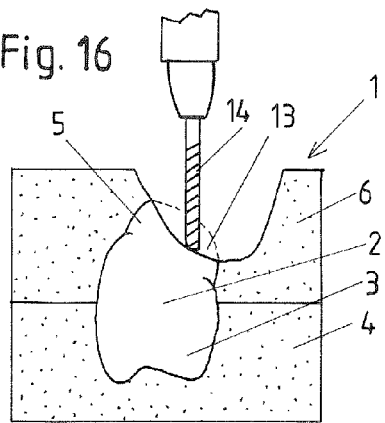
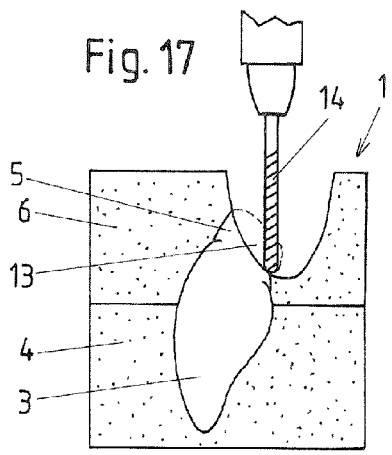

PROSTHETIC TOOTH SUPPORT

BACKGROUND

The present invention relates to a prosthetic tooth support with at least one prosthetic tooth, in particular with several prosthetic teeth. Moreover, the invention also relates to a kit having such a prosthetic tooth support, and to a method for machining at least one prosthetic tooth and a method for producing a prosthetic tooth support.

Total or partial dental prostheses are composed principally of at least two different components. These are, on the one hand, a prosthesis base, which replaces the missing gum areas, and, on the other hand, the prosthetic teeth, which function as replacements for the missing natural teeth of the patient. The prosthetic teeth are connected to the prosthesis base and have both therapeutic and also aesthetic functions. Prosthetic teeth are offered by various manufacturers. All commercially available prosthetic teeth are prefabricated forms which vary in terms of their color. Prefabricated tooth forms are commercially available in various sizes and are selected by the dental technician according to certain individual characteristics of the patient, e.g. available space, height, sex, and figure. The commercially available prosthetic teeth for use in total and partial prostheses in the patient's dentition are employed in a substantially unmachined state. For this purpose, the crown area in particular of the prosthetic teeth remains largely intact. However, in most cases the neck and root area of the prosthetic teeth have to be adapted on account of the different bite heights, that is to say the different distance between upper jaw and lower jaw in the individual patients. To this end, the neck and root areas of the prosthetic teeth are shortened. In the prior art, this is done free-hand by the dental technician, which results in inaccuracies and also in considerable expenditure of time, since the length of the prosthetic tooth has to be repeatedly checked. When shortening the teeth, the objective is to leave as much as possible of the neck of the tooth unmachined and to shorten it only by as little as possible. The neck and root area of the prosthetic tooth serves as a connection surface to the prosthesis base, although it also has important functions as regards the aesthetics of the prosthetic tooth and therefore of the entire prosthesis.

In dentistry in general, there has in recent years been an increase in the use of automated or computer-aided devices for the production of tooth replacements. In particular, the production of total prostheses presently represents a field of activity in the area of dental CAD-CAM development. This concerns both the design of the prosthesis base and also the positioning of the individual prosthetic teeth relative to the prosthesis base. For this reason, the information concerning the shape of the commercially available prosthetic teeth is also already digitized, i.e. provided as data records. However, for the digitally or virtually assembled or designed total prosthesis to be actually implemented in reality, it is still necessary for the commercially available prosthetic teeth to be shortened in order to find space in the prosthesis base.

In the prior art, the prosthetic teeth are made commercially available on prosthetic tooth supports, although the prosthetic teeth are affixed to the prosthetic tooth support so as to adhere only slightly via an adhesive compound. The adhesives used for this purpose serve simply to ensure that the prosthetic teeth are not lost during transport and are positioned for a better view. The adhesives are sufficiently weak so that the prosthetic teeth can be easily removed by hand from the prosthetic tooth support.

Moreover, the prosthetic teeth secured on the prosthetic tooth supports (so-called tooth cards) are fixed in the support medium of the support in the area of the neck of the tooth.

SUMMARY

The objective is to ensure that, for an automated machining step in milling devices controlled by means of data processors, prosthetic teeth can be positioned in such a way that the neck and root areas of the prosthetic teeth can be shortened in the desired way in an automated operation.

To meet this objective, it is proposed that a prosthetic tooth support of the type in question be modified such that a crown area of the prosthetic tooth or of the prosthetic teeth is embedded, preferably cast, at least partially, preferably completely, in a support layer.

It is therefore an underlying concept of the invention that the prosthetic tooth or the prosthetic teeth can be embedded or cast with their crown area in a support layer of the prosthetic tooth support according to the invention in such a way that the neck and root area of the prosthetic teeth protrudes from the support layer and can be machined or shortened by means of suitable milling devices known in the prior art, e.g. in the form of CNC milling machines. This allows the prosthetic teeth to be embedded in defined positions in the support layer. The defined positions in the prosthetic tooth support, and the information already available in digital form or to be created by scanning or other suitable means and concerning the tooth shape, can then be stored in a data record, preferably one based on a uniform system of coordinates, and can be fed to a data processor controlling the milling device.

In this sense, the invention also relates to a kit comprised of a prosthetic tooth support according to the invention and of a data record, wherein the data record contains the information concerning the shape and the position of the prosthetic tooth or of the prosthetic teeth in and on the prosthetic tooth support.

In order to ensure a secure hold during the machining, it is recommended that the prosthetic teeth be embedded in the support layer in a suitably firm but millable material, for example wax or plastic, which forms no chemical connection to the prosthetic tooth. Since the support layer completely fulfils the function of holding the prosthetic teeth in position, provision can be made, in a variant of the invention, that neck and root area of the prosthetic tooth or of the prosthetic teeth protrude at least partially, preferably completely, above the support layer and are freely visible.

In order to produce a prosthetic tooth support of this kind, a preferred method is one in which the prosthetic tooth or the prosthetic teeth is/are positioned with the neck and root areas in an auxiliary holding device, and then the crown area of the prosthetic tooth or of the prosthetic teeth is embedded, preferably cast or encapsulated, at least partially, preferably completely, in the support layer.

To be able to remove the prosthetic teeth from the support layer after the neck and root areas have been shortened, the support layer expediently has a predetermined breaking point. This predetermined breaking point can already be incorporated by the manufacturer or can be introduced into the support layer by the user with the aid of a milling device.

However, it is not essential that the neck and root area of the prosthetic tooth or of the prosthetic teeth are freely visible. Alternatively, provision can also be made that neck and root area of the prosthetic tooth or of the prosthetic teeth are embedded, preferably cast, at least partially, preferably completely, in a cover layer of the prosthetic tooth support.

In this variant, therefore, the one or more prosthetic teeth can be concealed completely in the prosthetic tooth support. This does not interfere with the machining or shortening, since the positions and the shapes of the prosthetic teeth are of course known from the aforementioned data record.

In a preferred method according to the invention for producing a prosthetic tooth support in which the neck and root areas are embedded in the cover layer, provision is made that the prosthetic tooth or the prosthetic teeth is/are positioned with the crown area in an auxiliary holding device, and then the neck and root area of the prosthetic tooth or of the prosthetic teeth are embedded, preferably cast, at least partially, preferably completely, in the cover layer of the prosthetic tooth support, after which the crown area of the prosthetic tooth or of the prosthetic teeth is embedded, preferably cast, at least partially, preferably completely, in the support layer.

To be able to secure the prosthetic tooth support safely and in a defined position in or on the milling device, preferred embodiments of the invention provide that a milling machine adapter of the prosthetic tooth support is secured on the support layer, which milling machine adapter protrudes preferably in a rod shape from the support layer and is used to secure the prosthetic tooth support in a milling device during a milling procedure. To avoid operating errors, the milling machine adapter preferably has form-fit indexing means, e.g. in its surface, to ensure that it can be secured in the milling machine only in a single and defined position. Such indexing means are known per se and can be provided in the form of notches, limit stops, polylines and the like.

If present, the cover layer should be made of a millable material. To ensure that the shortened prosthetic teeth can then also be removed from the support layer, the latter is expediently likewise comprised of a millable material. In principle, various plastics or waxes are suitable as such materials. In the sense of being millable, however, provision is expediently made that the support layer and/or the cover layer have/has or are/is comprised of a material having a Vickers hardness of between 10 HV and 200 HV. However, in expedient embodiments of the invention, the material of the support layer is at least as hard as or harder than the material of the cover layer.

With a kit according to the invention, already mentioned above and comprised of a prosthetic tooth support according to the invention and of the associated data record, a method according to the invention for machining at least one prosthetic tooth, preferably several prosthetic teeth, of a kit according to the invention is one in which the prosthetic tooth support of the kit is clamped, preferably by means of its milling machine adapter, in a milling device, and the data record of the kit is read into a data processor, and the milling device is controlled by the data processor to machine the prosthetic tooth or the prosthetic teeth on the basis of the data record. In this way, those regions of the neck and root area of the prosthetic teeth that are to be shortened in the prosthetic tooth support can be targeted under computer control and milled out. This allows computerized digital or virtual models of a dental partial prosthesis or total prosthesis to be converted to the real world, by means of the prosthetic teeth being shortened in the required manner for this purpose.

It is also possible to form additional grooves or channels in the prosthetic tooth during the described milling, which grooves or channels then function as protection against rotation or as additional retention for the prosthetic tooth in the prosthesis base.

If, during the construction of the prosthesis, it has been deemed necessary to shorten the prosthetic teeth also in the crown area, this manipulation of the teeth is also possible during the milling procedure, especially since the support layer, as has already been stated above, is expediently comprised of a millable material.

To ensure particularly good user-friendliness, provision can be made, in such a method, that the data record is stored in or on the prosthetic tooth support, preferably in or on the milling machine adapter, and is read in preferably automatically by the data processor before, during or after the clamping of the prosthetic tooth support in the milling device. The prosthetic tooth support can therefore itself have a data carrier, e.g. a transponder, barcode or the like, on which the data record is stored. This data carrier can be arranged on the milling machine adapter or at another suitable location on the prosthetic tooth support. The data processor can then read in the data record automatically or when requested, as soon as the prosthetic tooth support is clamped into the milling device.

For the sake of completeness, it will be noted that the data record of said kit according to the invention does not of course necessarily have to be arranged directly on the prosthetic tooth support. The data record can also be stored elsewhere and read into the data processor. For this purpose, numerous variants known per se are available in the prior art, and it is not necessary for all of these to be individually listed here.

For the sake of completeness, it will be noted that a prosthetic tooth is to be understood as an artificial tooth that is intended to be incorporated in a total or partial dental prosthesis. The crown area comprises the outer partial region of the prosthetic tooth that protrudes from the gum in a healthy natural tooth. The crown area comprises the masticatory or occlusal surface of the tooth. The neck and root area of a natural tooth are concealed within healthy gum. In the case of a prosthetic tooth, the neck and root area in the finished partial or total prosthesis is concealed at least for the most part within the prosthesis base. The neck and root area comprises the basal surface of the prosthetic tooth and serves to secure the prosthetic tooth in a corresponding recess in the prosthesis base.

Moreover, it will also be noted that suitable milling devices and data processors are known in the prior art in the form of a wide variety of CAD and CNC milling devices with corresponding computer control, and these need not be explained in any more detail here.

BRIEF DESCRIPTION OF THE DRAWINGS

Further features and details of preferred embodiments of the invention are explained in the following description of the figures, in which

FIGS. 6 to 8 show examples of a prosthetic tooth support according to the invention;

FIG. 9 shows a schematic representation of the machining, according to the invention, of the prosthetic teeth arranged in a prosthetic tooth support according to the invention;

FIGS. 10 to 15 show schematic representations of the production of a prosthetic tooth support according to the invention;

FIGS. 16 and 17 show schematic representations of the shortening of the prosthetic teeth arranged in the prosthetic tooth support according to the invention.

DETAILED DESCRIPTION OF THE PREFERRED EMBODIMENTS

Figure 1:
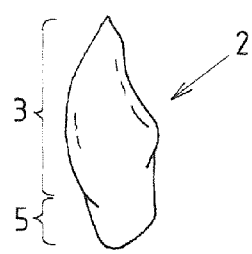
FIGS. 1 and 2 show examples of prosthetic teeth known per se in the prior art.
Figure 2:
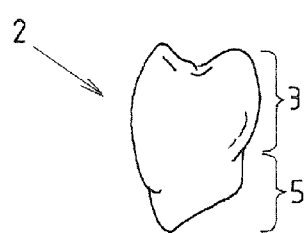
Figure 3:
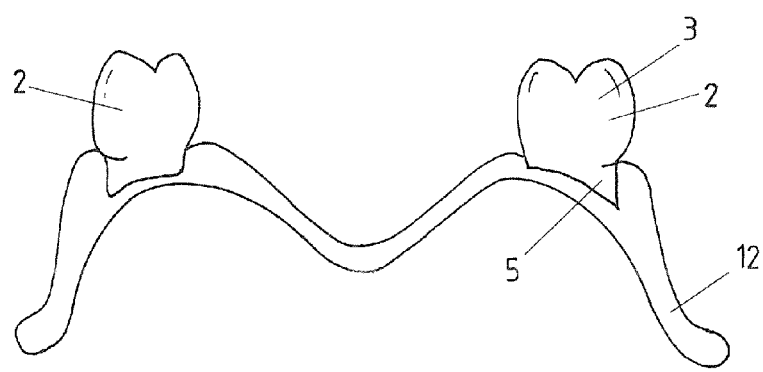
FIG. 3 shows the arrangement, known per se in the prior art, of these prosthetic teeth in a total prosthesis illustrated in cross section.
Figure 4:
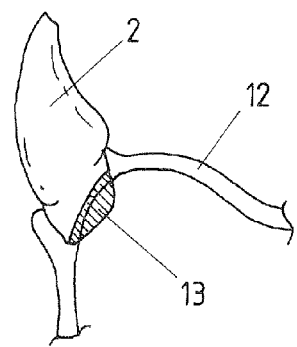
FIGS. 4 and 5 are views illustrating the need to shorten the prosthetic teeth.
Figure 5:
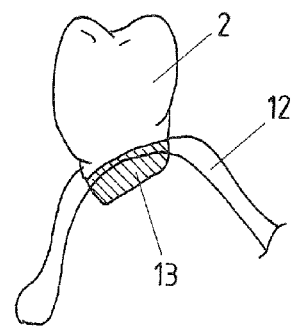

A prosthetic tooth 2 known per se in the prior art and also commercially available as such, specifically in the form of a front tooth, is shown diagrammatically in FIG. 1. An example of a prosthetic tooth 2 in the form of a molar is shown in FIG. 2. Both figures show the crown area 3 and the neck and root area 5 of the respective prosthetic tooth 2. FIG. 3 shows a cross section through a total prosthesis. In the prosthesis base 12, the prosthetic teeth 2 are secured in the corresponding recesses via their neck and root areas 5. The length of the neck and root area 5 determines how far the prosthetic tooth as a whole protrudes from the prosthesis base 12. The lower end of the neck and root area 5 forms, with the corresponding mating face of the prosthesis base 12, a suitable limit stop and the abutment face for the prosthetic tooth 2. The prosthetic teeth 2 are prefabricated products which are commercially available in a predefined shape and size. By contrast, the prosthesis base can be individually adapted to the jaw of the respective patient. To be able also to adapt the length of the respective prosthetic tooth 2 to the individual requirements of the patient, it is necessary, as has already been explained at the outset, to adapt the length of the respective prosthetic tooth to the space available in the prosthesis base. For this purpose, the length of a prosthetic tooth 2 has to be shortened. This has to be done by suitable removal of a partial region 13 of the neck and root area 5 of the tooth, as is illustrated schematically in FIGS. 4 and 5.

According to the invention, automation of this shortening operation is permitted by the use of prosthetic tooth supports 1, of which examples are shown in FIGS. 6 to 8. The prosthetic tooth supports 1 can contain one or more prosthetic teeth 2. Preferably, a prosthetic tooth support comprises four or eight molars or three or six front teeth. FIG. 6 shows a side view of a prosthetic tooth support 1 with a total of eight prosthetic teeth 2 provided as molar replacements. Only four of these prosthetic teeth 2 can be seen in the side view in FIG. 6. A plan view of the neck and root areas 5 of these prosthetic teeth 2 is shown in FIG. 8. Therefore, all eight prosthetic teeth 2 can be seen in FIG. 8.

FIG. 7 shows a side view which corresponds to FIG. 6, and in which three prosthetic teeth 2 provided as front tooth replacements are arranged. The prosthetic teeth 2 are each embedded with their crown areas 3 in the support layer 4 of the respective prosthetic tooth support 1 and are held firmly there. The cover layer 6, which embeds the neck and root areas 5, is optional. Although it is present in FIGS. 6 and 7, it can also be omitted, such that the neck and root areas 5 then protrude above the support layer 4 and are freely visible from the outside. For the sake of completeness, it will be noted that the support layer 4 and the cover layer 6 are shown as transparent in the figures, in order to see the prosthetic teeth 2. Of course, this transparency does not have to be provided in reality. The prosthetic teeth can also be concealed in the support layer 4, and in the optionally present cover layer 6, so as not to be visible from the outside.

A milling machine adapter 7 is secured on each of the prosthetic tooth supports 1 shown in FIGS. 6 to 8 and serves to clamp the prosthetic tooth support 1 in a milling device 10 known per se. The milling machine adapters 7 are expediently shaped and indexed in such a way that they can be secured exclusively in a single position in a corresponding seat of the milling machine. In FIGS. 6 to 8, this is achieved by the shoulder surfaces 18, which are provided for form-fit engagement in the milling device 10, and by the indexing lug 19.

In the sense of the kit according to the invention, the positions and shapes of the prosthetic teeth 2 in the prosthetic tooth support 1 are known and stored in the form of a data record 9. In this way, it is possible for the milling device 10, controlled by means of the data processor 11, to machine or shorten the neck and root areas 5 of the respective prosthetic teeth 2 according to the respective requirements, in a manner adapted to the total or partial prosthesis that is to be individually configured.

FIG. 9 is a schematic representation of a milling device 10 regulated and controlled by means of the data processor 11. Suitable milling devices 10 are known in the prior art, for example as CNC milling machines. The prosthetic tooth support 1 shown schematically in FIG. 9 is clamped, by means of its milling machine adapter 7, in the milling device 10. A schematically represented milling head 14 is provided for the machining or milling of the neck and root areas 5 and of the optionally present cover layer 6 of the prosthetic tooth support 1. Milling head 14 and prosthetic tooth support 1 can be positioned and adjusted relative to each other in a manner known per se, such that the milling head 14 can machine or mill all the desired areas of the prosthetic tooth support 1, particularly the neck and root areas 5 of the prosthetic teeth 2 arranged in the prosthetic tooth support 1, in the desired manner. The milling procedure performed by the milling device is controlled by means of the data processor 11. The position and shape of the prosthetic teeth 2 in the respective prosthetic tooth support 11 are contained in the data record 9, which is read in by the data processor 11 in a suitable way. By means known per se, the data processor 11 is additionally supplied with the target values 20 that define the extent to which the one or more prosthetic teeth 2 have to be machined or shortened. With an arrangement shown schematically in FIG. 9, it is possible to carry out the method mentioned at the outset for machining the one or more prosthetic teeth. FIG. 9 shows a schematic representation of a common system of coordinates 15, on the basis of which the data processor 11 works and on the basis of which the information concerning the position and shape of the prosthetic tooth 2 or of the prosthetic teeth 2 in the prosthetic tooth support 1 is also stored in the data record 9. The milling head 14 can be used not only to machine or mill the neck and root areas 5 and the optionally present cover layer 6. Preferably, a suitable predetermined breaking point can also be milled into the support layer 4 by means of the milling head 14, so as to be able to remove the prosthetic teeth 2 from the prosthetic tooth support 1 after the machining of the neck and root areas 5 and, if appropriate, of the crown areas has been completed. However, predetermined breaking points of this kind can of course also be incorporated into the prosthetic tooth support 1 beforehand by the manufacturer.

FIGS. 10 to 15 illustrate by way of example a method for producing a prosthetic tooth support 1 according to the invention. FIGS. 10, 12 and 14 show individual steps using the example of a prosthetic tooth 2 designed as a molar, while FIGS. 11, 13 and 15 show the same using the example of a prosthetic tooth 2 provided as a front tooth. As has already been explained at the outset, the prosthetic teeth 2 are commercially available in the form shown. They are brought into a defined position and held there by means of a suitable auxiliary holding device. This is illustrated in FIGS. 10 and 11. In both figures, the auxiliary holding devices 8 are comprised of two holding jaws 16 that can be moved away from and toward each other. In FIGS. 10 and 11, the respective prosthetic tooth 2 is already positioned and held between the holding jaws 16 in the respective holding device 8, as a result of which the position of the respective prosthetic tooth 2 in the system of coordinates 15 is known. The auxiliary holding devices 8 can have different numbers of seats for different numbers of prosthetic teeth 2. The number is expediently adopted in each case according to the prosthetic tooth support to be produced and according to the number of prosthetic teeth 2 provided therein.

For the sake of completeness, it will be noted that, with a suitable shape of the prosthetic teeth 2, the auxiliary holding devices 8 do not necessarily have to be designed in two or more parts. However, this is generally preferable. For example, the teeth can also be fixed in one-part molds, by means of suction mechanisms in the mold.

FIGS. 12 and 13 show the next method step. Firstly, the prosthetic tooth 2 and the auxiliary holding device 8 are encased by means of the casing 17. The cover layer 6 is then cast or injected, as a result of which a partial region of the prosthetic teeth 2 protruding above the holding device 8 is embedded in the cover layer 6. The entire neck and root area 5 of the prosthetic tooth or of the prosthetic teeth 2 should preferably be located in the cover layer 6. However, parts of the crown area 3 can also be located in the cover layer 6. The crown area 3 must be embedded in the support layer 4 only to such an extent that the respective prosthetic tooth 2 is held sufficiently firmly for machining by means of the milling head 14. The auxiliary holding device 8 can be removed after hardening of the cover layer 6, which is preferably comprised of a suitable millable plastic or wax. The prosthetic teeth 2 are then held in the correct position in the cover layer 6. After removal of the auxiliary holding device 8, the support layer 4 can then be cast, or introduced in some other suitable way, such that the crown area of the prosthetic tooth 2 or of the prosthetic teeth 2 is embedded in the support layer 4. After the material of the support layer 4 has hardened if necessary, the casing 17 can be removed. Thereafter, if necessary, the milling machine adapter 7 can be mounted on the prosthetic tooth support 1. FIGS. 16 and 17 show schematically how the prosthetic tooth support 1 prepared in this way is machined by means of the milling head 14 after being clamped in the milling device 10, wherein the cover layer 6 and the partial region 13 of the neck and root area 5 to be removed are milled off to the required extent in accordance with the criteria of the data processor 11.

FIGS. 10 to 17 relate to an illustrative embodiment in which the prosthetic tooth support 1 has both a carrier layer 4 and also a cover layer 6.

However, as has already been explained at the outset, the cover layer 6 is not absolutely essential. In order to produce a prosthetic tooth support 1 without cover layer 6, the production method explained with reference to FIGS. 10 to 15 can be modified in the sense that the prefabricated prosthetic teeth 2 are positioned not with their crown area 3 but instead with their neck and root area 5 in a suitably shaped auxiliary holding device 8 containing the position data. A suitable casing 17 can then be mounted on the auxiliary holding device 8. Thereafter, the support layer 4 is introduced directly or cast, and in this way the regions of the crown area 3 of the prosthetic teeth 2 protruding above the auxiliary holding device 8 are embedded. After removal of the casing 17 and of the auxiliary holding device 8, a support layer 4 with prosthetic teeth 2 arranged therein is then produced in which the neck and root areas 5 protrude freely above the support layer 4 and can be machined accordingly by means of a suitable milling head 14 in a milling device 10.

KEY TO THE REFERENCE NUMBERS 1 prosthetic tooth support
2 prosthetic tooth
3 crown area
4 support layer
5 neck and root area
6 cover layer
7 milling machine adapter
8 auxiliary holding device
9 data record
10 milling device
11 data processor
12 prosthesis base
13 partial region to be removed
14 milling head
15 system of coordinates
16 holding jaw
17 casing
18 shoulder surface
19 indexing lug
20 target values

The invention claimed is:

1. A kit comprising a prosthetic tooth support and a data record fixed in a tangible medium, wherein:
the prosthetic tooth support comprises at least one prosthetic tooth having a crown area, the crown area of the at least one prosthetic tooth being cast or encapsulated at least partially in a support layer, and
the data record contains information concerning a shape and a position of the at least one prosthetic tooth in or on the prosthetic tooth support.

2. The kit as claimed in claim 1, wherein a neck and root area of the at least one prosthetic tooth protrudes at least partially above the support layer and is freely visible.

3. The kit as claimed in claim 1, wherein a neck and root area of the at least one prosthetic tooth is embedded at least partially in a cover layer of the prosthetic tooth support.

4. The kit as claimed in claim 1, further comprising a milling machine adapter for the prosthetic tooth support that is secured on the support layer, said milling machine adapter is used to secure the prosthetic tooth support in a milling device during a milling procedure.

5. The kit as claimed in claim 3, wherein at least one of the support layer or the cover layer has or is comprised of a material having a Vickers hardness of between 10 HV and 200 HV.

6. A method for machining at least one prosthetic tooth of a kit as claimed in claim 1, wherein the prosthetic tooth support of the kit is clamped in a milling device, and the data record of the kit is read into a data processor, and the milling device is controlled by the data processor to machine the at least one prosthetic tooth based on the data record.

7. The method as claimed in claim 6, wherein the data record is stored in or on the prosthetic tooth support and is read by the data processor during
or after the clamping of the prosthetic tooth support in the milling device.

8. A method for producing a prosthetic tooth support of a kit as claimed in claim 2, comprising positioning the at least one prosthetic tooth with the neck and root area in an auxiliary holding device, and then embedding casting or encapsulating the crown area of the at least one prosthetic tooth at least partially in the support layer.

9. A method for producing a prosthetic tooth support of a kit as claimed in claim 3, comprising positioning the at least one prosthetic tooth with the crown area in an auxiliary holding device, and then embedding the neck and root area of the at least one prosthetic tooth at least partially in the cover layer of the prosthetic tooth support, and embedding casting or encapsulating the crown area of the at least one prosthetic tooth at least partially in the support layer.

10. The kit as claimed in claim 1, wherein the crown area is completely cast or encapsulated in the support layer.

11. The kit as claimed in claim 2, wherein the neck and root area extends completely above the support layer.

12. The kit as claimed in claim 3, wherein the at least one prosthetic tooth is cast or encapsulated completely in the cover layer.

13. A method for machining at least one prosthetic tooth as claimed in claim 6, wherein the prosthetic tooth support is clamped by means of its a milling machine adapter in the milling device.

14. The kit as claimed in claim 4, wherein said milling machine adapter protrudes in a rod-shape from the support layer.

15. The method as claimed in claim 7, wherein the data record is stored in or on the milling machine adapter.

16. The method as claimed in claim 7, wherein the data record is read automatically by the data processor.

\* \* \* \* \*